United States Patent [19]

Flint et al.

[11] Patent Number: 4,929,441

[45] Date of Patent: May 29, 1990

[54] UNNATURAL SEX ATTRACTANTS FOR MALE PINK BOLLWORMS AND PINKSPOTTED BOLLWORMS AND USE THEREOF

[75] Inventors: Hollis M. Flint; John R. Merkle, both of Tempe, Ariz.

[73] Assignee: The United States of America as represented by the Secretary of Agriculture, Washington, D.C.

[21] Appl. No.: 800,891

[22] Filed: Nov. 20, 1985

Related U.S. Application Data

[63] Continuation of Ser. No. 600,259, Apr. 13, 1984, abandoned.

[51] Int. Cl.$^5$ ............................................. A01N 25/00
[52] U.S. Cl. ...................................................... 424/84
[58] Field of Search ........................................... 424/84

[56] References Cited

U.S. PATENT DOCUMENTS 3,586,712  6/1971  Green et al. ........................... 424/84

OTHER PUBLICATIONS

Chemical Abstracts/98:174784x (1983).
Chemical Abstracts 100:20496z (1984).
Chemical Abstracts 100:18730z (1984).
Chemical Abstracts 85:117931g (1976).
Flint et al., *Environmental Entomology* 6(2):274–275 (1977).
Flint et al., *Journal of Economic Entomology* 71(4):664–666 (1978).
*Webster's Seventh New Collegiate Dictionary*, p. 543.

*Primary Examiner*—Allen J. Robinson
*Attorney, Agent, or Firm*—M. Howard Silverstein; John D. Fado; Margaret A. Connor

[57] ABSTRACT

Novel sex attractant compositions for the adult male pink bollworm or pinkspotted bollworm containing an unnatural ratio of Z,Z- and Z,E-isomers of 7,11-hexadecadien-1-ol acetate and use thereof are described. In the method of the invention, the novel unnatural attractant compositions are applied to fields treated with the Z,Z- or Z,E-isomer of 7,11-hexadecadien-1-ol acetate. This causes the preference of the males to be shifted away from the ratio of the isomers in the pheromone emitted by the female of the species and to the unnatural attractant compositions.

14 Claims, 1 Drawing Sheet

UNNATURAL SEX ATTRACTANTS FOR MALE PINK BOLLWORMS AND PINKSPOTTED BOLLWORMS AND USE THEREOF

This application is a continuation of application Ser. No. 600,259 filed Apr. 13, 1984, now abandoned.

BACKGROUND OF THE INVENTION

1. Field of the Invention

This invention relates to novel unnatural sex attractant compositions and use thereof to attract pink bollworms and pinkspotted bollworms in fields treated with the Z,Z- or Z,E-isomer of 7,11-hexadecadien-1-ol acetate. More particularly, the invention provides means for altering the preference of the male pink bollworm or pinkspotted bollworm away from the sex pheromone emitted by the female of the species and to the novel compositions of the invention.

2. Description of the Prior Art

The pink bollworm, *Pectinophora gossypiella* (Saunders) is an economically important field pest afflicting cotton production throughout the world. The pink bollworm larvae feed on buds, flowers, and bolls of the cotton plant, and because of their widespread distribution, voracious appetite, and enormous population cause severe economic losses to cotton growers.

While chemical pesticides are useful in the control of the pink bollworm, use of widespread broadcasting of insecticides has the disadvantages of destruction of desirable predators and parasites which aid in the control of *Heliothis virescens*, particularly when used early in the growing season; development of insecticide-resistant pink bollworm populations; toxicity to man and animals; contamination of the environment, and expense of application.

The continued search for alternatives to the widespread application of insecticides has led to the investigation of sex attractants as agents for use in integrated pest management programs. A number of economically important insects are currently monitored, partially controlled, or completely controlled by use of their own specific pheroaone.

The pink bollworm sex pheromone has been identified as about a 1:1 mixture of the Z,Z- and Z,E-isomers of 7,11-hexadecadien-1-ol acetate, hereinafter termed gossyplure (*Science* 181:873–875 (1973)). Gossyplure has been successfully used for sexual communication disruption between adult moths resulting in the reduction of larvae infesting cotton bolls (*Science* 196:904–905 (1977)). Gossyplure is theorized to work in either of two ways (1) false trail following wherein males spend their time following pheromone trails released from the applied sources and (2) adaptation of the antennal receptor sites or habituation of the central nervous system (CNS). To be effective for false trail following, the applied sources must be in numbers far exceeding the numbers of female pink bollworms that are emitting the pheromone such that the chance of a male finding a female instead of a source is low and the emission rate of the sources must be high enough to be conspicuous in the low ambient background of gossyplure from all the other sources. In the adaptation and habituation responses, it is theorized that if enough gossyplure is released into the atmosphere, the antennal receptor sites become adapted and fail to send out the usual electrical signal. Also, when the antennal receptor sites are continually sending electrical impulses to the CNS, the CNS becomes habituated and the insect may no longer respond with the normal behavior.

The primary disadvantages of using gossyplure sources are (1) that males are seeking gossyplure-emitting sources and thus may encounter female moths (that also emit gossyplure) and mate, and (2) that reduction of mating is not sufficient, particularly when populations of the pink bollworm are greater than ten percent in the cotton bolls. While use of an insecticide in combination with gossyplure improves the efficacy through the debilitation or killing of male moths attracted to the pheromone-baited dispensers and contacting the insecticide, there have been problems attaining the desired efficacy of annihilation, i.e., removal of 95% of the males, with this method. Additionally, since the males are seeking gossyplure-emitting sources, they may encounter females and mate.

Flint and Merkle (*Journal of Economic Entomology* 76:40–46 (1983)) disclose the use of the individual component isomers of gossyplure to disrupt sexual communication between male and female pink bollworm moths as determined by reduction in trap catch and mating in field plots. Because males do not usually contact sources of individual component isomers of gossYplure, the combining of an individual isomer with an insecticide has little or no value in annihilation of the male moth.

The pinkspotted bollworm, *Pectinophora scutigera* (Holdaway), is associated with various native malvaceous plants in Australia and the adjacent Pacific region and is also the primary pest of cotton in central Queensland. Because the area for cotton growing in Queensland and northern New South Wales has been significantly increased recently, there is concern that the pinkspotted bollworm may be transmitted outside its present limited range and become a more serious problem (Rothchild, *Journal of the Australian Entomological Society* 22:161–166 (1983)). While the components of the pinkspotted bollworm pheromone are not known with certainty, trap catch data suggests that it is about 10:1 ratio of Z,Z- to Z,E-isomer of 7,11-hexadecadien-1-ol acetate (Rothchild, *Environmental Entomology* 4:983–985 (1975)). Use of sex attractants having a composition or attraction properties similar to that of the natural pheromone to monitor or control the pinkspotted bollworm has the disadvantage that the males may encounter female moths and mate.

SUMMARY OF THE INVENTION

We have now for the first time discovered a method wherein the preference of male pink bollworm or pinkspotted bollworm moths is shifted from the ratio of Z,Z-7,11-hexadecadien-1-ol acetate (Z,Z-isomer):Z,E-7,11-hexadecadien-1-ol acetate (Z,E-isomer) which occurs in the pheromone of the species (natural ratio) to other ratios of the isomers (unnatural ratios). In the case of the pink bollworm, the preference of the male moths is shifted away from the 1:1 ratio of Z,Z- to Z,E-isomer (gossyplure), thus unlike males in gossyplure-treated fields, pink bollworm males are no longer seeking females that emit the 1:1 ratio. Similarly, with our invention male pinkspotted bollworm moths no longer seek the pheromone emitted by the female of the species. Such an alteration of male pink bollworm or pinkspotted bollworm preference to compositions comprising unnatural ratios of the pheromone components has not been reported prior to our invention.

The novel unnatural sex attractant compositions of the invention comprise a ratio of the Z,Z- to Z,E-isomers of 7,11-hexadecadien-1-ol acetate which is different from that naturally occurring in the pheromone emitted by the female of the species. In the method of the invention, these novel unnatural attractant compositions are applied to fields treated with the Z,Z- or Z,E-isomer of 7,11-hexadecadien-1-ol acetate. This causes the male of the species to seek out the unnatural attractant compositions in preference to the pheromone emitted by the female of the species.

The primary advantage of the invention is that the preference of male pink bollworm and pinkspotted bollworm moths is shifted away from the ratio of the isomers which is emitted by female moths, thus the likelihood that the males will mate is greatly reduced. Another advantage of the invention is that the novel compositions can be used in conjunction with insecticides or other biological control agents for annihilation of male moths.

The usefulness of the unnatural attractant compositions to elicit a novel behavioral response in the method of the invention when applied to a locus of pink bollworm or pinkspotted bollworm males suggests the following economic applications: (1) the control of reproduction in adult populations either by direct disruption of mating through confusing or inhibitory properties, or by attracting a demographically significant portion of the male population for subsequent destruction and (2) the monitoring of male populations in fields treated with the Z,Z- or Z,E-isomer.

In accordance with this discovery, it is an object of the invention to provide "unnatural" attractants for adult male pink bollworms and pinkspotted bollworms in fields treated with the Z,Z- or Z,E-isomer such that males are no longer attracted to pheromone-emitting sources such as female bollworms of the species.

A further object of the invention is the use of the unnatural attractants in combination with traps, insecticides, or biological control agents so that males seeking the attractants are incapacitated or destroyed.

A still further objective is to provide unnatural attractant compositions for monitoring populations of male pink bollworm or pinkspotted bollworm moths in fields treated with the Z,Z- or Z,E-isomer of 7,11-hexadecadien-1-ol acetate.

Other objects and advantages of the invention will become readily apparent from the ensuing description.

DETAILED DESCRIPTION OF THE INVENTION

Figure 1:
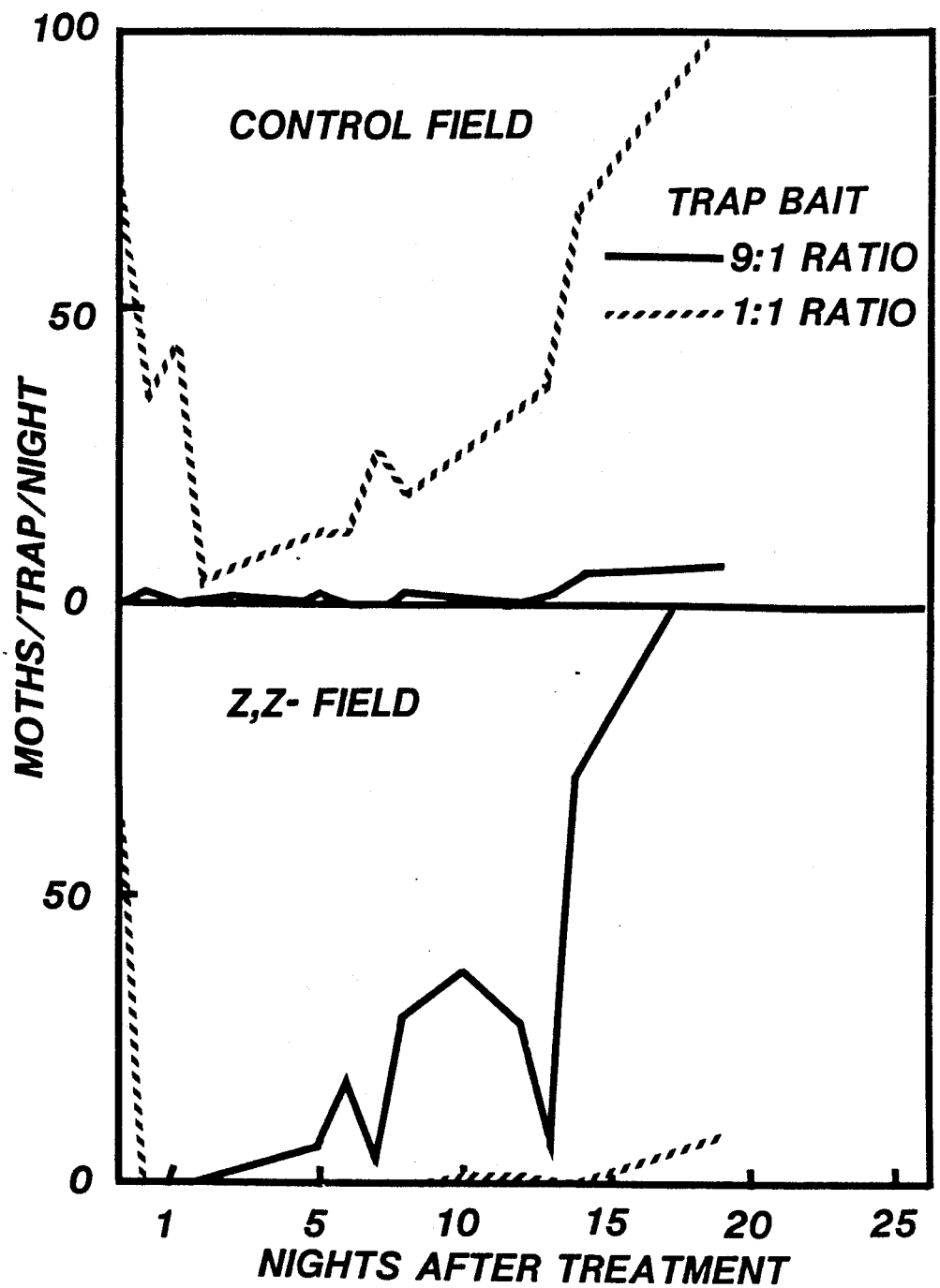
FIG. 1 shows catches of male pink bollworm moths in traps baited with either the 9:1 or 1:1 ratios of Z,Z- to Z,E-isomers in a field treated with the Z,Z-isomer or left untreated.

As stated above, the novel unnatural sex attractant compositions of the invention comprise the Z,Z- and Z,E-isomers of 7,11-hexadecadien-1-ol acetate combined in a ratio different from that naturally occurring in the pheromone emitted by the female of the species. In the method of the invention, these novel unnatural attractant compositions are applied to fields treated with the Z,Z- or Z,E-isomer of 7,11-hexadecadien-1-ol acetate. With this method, the preference of male pink bollworm or pinkspotted bollworm moths is shifted away from the ratio of Z,Z- to Z,E-isomer which naturally occurs in the pheromone secretion of the female of the species and to the novel compositions of the invention, thus the likelihood that males will encounter female moths and mate is greatly reduced.

In the case of the pink bollworm, the field treatment can be with either the Z,Z- or Z,E-isomer. The unnatural attractant compositions comprise a mixture of Z,Z- and Z,E-isomers in a ratio of about 75:25 to about 99:1 on a volume basis and preferably from about 90:10 to 99:1. Where the field treatment is with the Z,Z-isomer, the major component of the unnatural attractant composition (unnatural ratio) is the Z,Z-isomer. Similarly, where the field treatment is with the Z,E-isomer, the major component of the unnatural attractant composition ratio is the Z,E-isomer.

In the case of the pinkspotted bollworm, the isomer used for the field treatment is the Z,E-isomer. The unnatural attractant compositions comprise a ratio of Z,Z- to Z,E-isomer in a range of about 3:1 to 1:9 on a volume basis and preferably from about 1:1 to 1:3.

Individual Z,Z- and Z,E-isomers of 7,11-hexadecadien-1-ol acetate for use for the field treatment and for preparation of the unnatural attractant compositions are available commercially or may be synthesized as described by C.A. Hendrick in "The Synthesis of Insect Sex Pheromones," *Tetrahedron* 33:1845–1889 (1977).

In accordance with the invention, Z,Z- or Z,E-isomer is applied to the area to be treated in an effective amount, that is, in an amount sufficient to permeate the atmosphere and achieve the alteration of male bollworm preference. The optimum amount of Z,Z- or Z,E-treatment will vary depending on the emission rate of the substrate. The effective amount of isomer treatment can be readily determined by placing traps baited with ratios of Z,Z- to Z,E-isomer approximating that found in pheromone of the species and seeing if the trap catch is significantly diminished. For example, an effective amount of isomer would cause the catches of male pink bollworm moths in Delta traps baited with 1 mg of gossyplure to be reduced to zero moths per trap per night or close to zero. The isomer treatment may be applied in different ways known in the art of dispensing pheromones, for example by aerial dissemination, ground application, and the like, using any type of trap or pheromone dispenser known in the art, such as flake dispensers, hollow fibers, or microcapsules. If desired, the isomer formulation may be metered onto the field together with a commercial adhesive carrier.

The novel attractant compositions, (unnatural ratios) described above are applied to the field using any pheromone dispenser and application procedure known in the art. Typically, the attractant composition would be applied to the dispenser in solution with hexane, methylene chloride or other suitable carrier. Application of the unnatural attractant compositions may be prior to, simultaneously with, or after the field treatment with the Z,Z- or Z,E-isomer.

As previously discussed, the attractant composition may be used either as a monitoring agent or control agent for adult pink bollworms or adult pinkspotted bollworms in fields treated with the Z,Z- or Z,E-isomer. In practice, the attractant composition is applied to a locus of the adult insects in an amount effective to induce the desired male response. In the case of an attractant response, an effective amount is defined as that quantity of agent which attracts male bollworm moths to the location of a bait at a rate significantly higher than males are attracted to a nonbaited location. Where it is desired that the attractant compositions of the invention be used as control agents in conjunction with insecticides, an effective amount of the insecticide is applied, that is, an amount which is lethal for an exposed insect or at least sublethal but sufficient to incapacitate the insect in regard to mating activity. One suitable commercial treatment for controlling the bollworm in accordance with this invention comprises the aerial distribution of an effective amount of Z,Z- or Z,E-isomer in a dispenser substrate, e.g. flakes or fibers, together with a percentage of substrates containing the unnatural attractant composition and an insecticide.

In addition to insecticides, the attractants of the invention may be formulated with other materials, for example, feeding adjuvants chemosterilants, and the like. Slow release may be effected by encapsulation or absorption into a porous substrate. Additionally, the attractant compositions may be applied along with an adhesive carrier.

The following examples are intended to further illustrate the invention and are not intended to limit the scope of the invention which is defined by the claims.

EXAMPLES

The attractive properties of the novel compositions of the invention toward male pink bollworm moths were tested under field conditions in field plots treated with Z,Z-isomer, gossyplure or untreated (Examples 1-4) or Z,E-isomer (Example 5). The test fields were planted to short staple cultivars of cotton, *Gossypium hirsutum* L., and received the usual cultural practices of the farm managers. The attractive properties of the invention toward male pinkspotted bollworm moths were tested in field plots treated with Z,Z-isomer, Z,E-isomer, or untreated (Example 6).

EXAMPLE 1

The attractant properties of ratios of 1:0, 9:1, 3:1, 1:1, 1:3, 1:9, and 0:1 (Z,Z-isomer: Z,E-isomer) toward male pink bollworm moths in fields treated with Z,Z-isomer only, gossyplure only, or untreated were tested in 4-16 ha field plots near Phoenix, AZ as follows: Gossyplure (commercially prepared 1:1 ratio) or the Z,Z-isomer was dispensed aerially into the fields using a three layer laminate flake, 0.32 cm$^2$, comprising gossyplure or the Z,Z-isomer as the middle layer between two layers of vinyl plastic as described in Henneberry et al. (*Journal of Economic Entomology* 74:376 (1981)). The gossyplure-containing flake was formulated as the Hercon "Disrupt" product produced by the Hercon Group of Herculite Products, Inc., New York, NY and contained 10 mg/2.54 cm$^2$ of gossyplure composed of 48.5% Z,E-isomer, 47.8% Z,Z-isomer, and 3.7% unspecified, non-pheromonal. Z,Z-isomer was obtained from Chemsampco, Columbus, OH and contained 96% Z,Z-isomer, less than 1.8% Z,E-isomer, and 2.2% unspecified, non-pheromonal. The Z,Z-isomer containing flake was prepared identical to the gossyplure flake product except that it contained 20 mg Z,Z-isomer/2.54 cm$^2$. For application, the flake formulations were metered together with a commercial adhesive carrier, "Phero-tac 65," produced by Hercon. Application rates were 6.9-15.3 g active ingredient (AI)/ha of Z,Z-isomer and 2.8-3.7 g AI/ha of gossyplure.

Test baits were prepared by placing 1 mg amounts of the test ratios in 50 ul of methylene chloride and applying the mixture to rubber sleeve stoppers as described by Flint et al. (*Journal of Economic Entomology* 67:738-740 (1974)). The Z,Z-and Z,E-isomers used to prepare the test baits were obtained from Farchan Chemical Co., Willoughby, OH and had the following compositions: Z,Z-isomer, 98.8% Z,Z-isomer and 1.2% Z,E-isomer; Z,E-isomer, 96.9% Z,E-isomer, 2.1% Z,Z-isomer, and 0.9% unspecified, non-pheromonal. The 1:1 ratio used was gossYplure having the composition described above. The test baits were placed in commercial Delta traps as described by Flint and Merkle (*Southwestern Entomologist* 8:140-144 (1983)) and deployed in 20- to 40-m grids placed above the canopy (top foliage) of the cotton plants. Each test consisted of two sets of 10 traps per ratio. Each row of traps contained all treatments in random order. The traps were placed in the fields 1-9 days after aerial treatment and left in the field 1-13 days. The tests were conducted in fields not yet under insecticidal control programs.

Analysis of variance was used to test for significance. Duncan's multiple range test was used to partition means into significant ranges when a significant F value ($P=0.05$) was found by analysis of variance.

The results of the tests (Table I) indicate a significant alteration of the preference of males for ratios containing a predominance of the Z,Z-isomer (unnatural ratio) in fields treated with this isomer. Males in untreated fields or in fields treated with gossyplure preferred the 1:1 (natural) ratio. The data also indicate that in a field treated with the Z,Z-isomer, trap baits must contain some Z,E-isomer in order to be attractive; the Z,Z-isomer only was not attractive.

TABLE I

| Treatment in field | No. of tests | % of total catch for indicated ratio (Z,Z-:Z,E-)[1] | | | | | | |
|---|---|---|---|---|---|---|---|---|
| | | 1:0 | 9:1 | 3:1 | 1:1 | 1:3 | 1:9 | 0:0 |
| Gossyplure | 4 | 0 b | 0 b | 17 b | 78 a | 5 b | 0 b | 0 b |
| Z,Z-isomer | 5 | 0 c | 69 a | 28 b | 3 c | 0 c | 0 c | 0 c |
| Untreated | 5 | 0 d | 5 c | 27 b | 66 a | 2 cd | 0 d | 0 d |

[1]Means within a row followed by a common letter are not significantly different ($P = 0.05$) by Duncan's multiple range test.

EXAMPLE 2

The attractive properties of test compositions containing ratios of 9:1, 1:1, and 1:9 Z,Z-:Z,E-isomer in test fields treated with gossyplure alone, Z,Z-isomer alone, or untreated were tested during August and September in two farms near Phoenix, AZ. The procedure was the same as described in Example 1, with the exception that the baited traps containing 1 mg baits were put out in the fields 4 and 6 weeks after aerial application of gossyplure, or Z,Z-isomer, after the initiation of insecticide programs, to study the longevity of the effects of treatments with 9:1, 1:1, and 1:9 ratio preferences. The test fields received three treatments at approximately 14-day intervals prior to the beginning of the post-treatment period. The traps, which were deployed in 30-m grids, were left in the fields one night only because of the large populations of pink bollworm moths The results of the test (Table II) indicate that a significant preference of males for the Z,Z-predominant (9:1) ratio persisted 4 and 6 weeks after treatment with the Z,Z-isomer. As in the test of Example 1, the 1:1 ratio was significantly preferred in the gossyplure-treated and untreated fields.

TABLE II

| Treatment in field | Weeks Post-treatment | Avg. males/trap at indicated ratio[1] | | |
|---|---|---|---|---|
| | | 9:1 | 1:1 | 1:9 |
| *Johnson farm* | | | | |
| Gossyplure | 4 | 0 b | 21 a | 0 b |
| Z,Z-isomer | | 60 a | 3 b | 1 c |
| Untreated | | 22 b | 89 a | 0 c |
| *Evans farm* | | | | |
| Gossyplure | 6 | 9 b | 95 a | 1 b |
| Z,Z-isomer | | 147 a | 39 b | 3 c |
| Untreated | | 25 b | 151 a | 6 c |

[1]Means within a row followed by a common letter are not significantly different (p = 0.05) by Duncan's multiple range test.

EXAMPLE 3

The effect of dose rate on the catch of males baited in traps baited with gossyplure or with the 9:1 (Z,Z:Z,E) ratio in fields treated with Z,Z-isomer or gossyplure or untreated was tested as described in Example 1, except that the baits contained dose rates of 0, 0.01, 0.1, 1.0, and 10 mg of the test ratio. The baits were placed in the field mid-season (June, July and August) 11–13 days after aerial treatment (Test 1) and late in the season (September) one day after aerial treatment. (Test 2). Tests were for one night. In the latter test, fields were treated only with the Z,Z-isomer. Both series of tests were conducted in fields not yet under insecticidal control programs.

The results of the test (Table III) showed that increasing the dose rate of the 9:1 ratio of Z,Z- to Z,E-isomers from 0.1 mg to 10 mg/bait significantly increased the capture of males in fields treated with the Z,Z-isomer (Test 1). Traps baited with the same doses of the 9:1 ratio were relatively unattractive in gossyplure-treated or untreated fields.

A side-by-side test of gossyplure and 9:1 ratio baits containing 0.1–10 mg/bait in fields treated with the Z,Z-isomer indicated that the 9:1 ratio baits caught 20–98% more moths than gossyplure baits, depending on the dose. These results indicate that the 10 mg 9:1 bait was the most effective one for capture of male moths in fields treated with the Z,Z-isomer.

TABLE III

| Treatment in field | Material in trap | Avg. catch/trap baited with indicated mg of material[1] | | | | |
|---|---|---|---|---|---|---|
| | | 0.01 | 0.1 | 1.0 | 10.0 | 0 |
| *Test 1, avg. 3 tests* | | | | | | |
| Gossyplure | 9:1 ratio | 0 b | 0 b | 0.2 b | 0.7 a | 0 b |
| Z,Z-isomer | 9:1 ratio | 0.1 c | 1.6 c | 11.1 b | 65.9 a | 0 c |
| Untreated | 9:1 ratio | 0 b | 0.1 b | 0.6 ab | 1.5 a | 0 b |
| *Test 2, avg. 2 tests* | | | | | | |
| Z,Z-isomer | 9:1 ratio | | 0.5 c | 26.9 b | 139.3 a | |
| Z,Z-isomer | Gossyplure | | 0.4 b | 0.7 b | 3.1 a | |

[1]Means within a row followed by the same letter are not significantly different (P = 0.05) by Duncan's multiple range test.

EXAMPLE 4

Population of the male pink bollworm may be monitored in fields treated according to the invention as indicated by the results of the following experiment. Two 4 ha fields situated 1 km apart near Phoenix, AZ, and having no insecticide treatment, were treated as follows. One field was treated with 15.3 g AI Z,Z-isomer/ha and the other (control) field was untreated. One day prior to the Z,Z-treatment, traps baited with 1 mg of either gossyplure or the 9:1 ratio of Z,Z to Z,E-isomer were placed about 20 m inside each field and separated from each other by 15 m. Four traps for each type of bait, one per quadrant, were used in each field. The trap catches in the two fields were recorded 5 to 6 days/week for 18 days. The results are shown in FIG. 1. In the Z,Z-treated field, traps baited with the 9:1 ratio caught 14 times more male moths than gossyplure. In the untreated control field, gossyplure caught 20 times as many males as the unnatural (9:1) attractant during the test period.

EXAMPLE 5

The preference of male pink bollworm moths is shifted away from the 1:1 mixture of Z,E- to Z,Z-isomers (gossyplure) and to a mixture which contains predominately the Z,E-isomer in fields treated with the Z,E-isomer. For this test rubber stoppers, treated with 5 mg each of the Z,E-isomer, were applied to cotton plants in a 0.1 ha field plot. The stoppers were pinned to the tops of plants in a 1 m×2 m grid (rate of ca. 12,800 stoppers containing 64 g AI/ha). The halflife for emission from the stoppers is about 100 days which is ca. 10 times slower than flake formulations. The release rate was then roughly comparable to 6.5 g AI/ha in flakes. The stoppers were placed in the plot on a farm in Tempe, AZ, together with the ratio test. The ratio test was made up of 3 Delta traps for each of the following ratios (Z,Z-:Z,E-): 1:0, 9:1, 3:1, 1:1, 1:3, 1:9, 0:1. Each bait contained 1 mg of the test ratio. Traps were placed in 3 rows of 7 traps each (7 m×10 m grid) within the treated area. A duplicate ratio test was placed in the opposite end of the same field, ca. 200 m from the treated plots, to serve as a control. All traps were checked daily for 2 weeks.

Treatment of a field plot with the Z,E-isomer of gossyplure resulted in a significant shift of the preference of male moths from the 1:1 ratio to ratios containing a higher percentage of the Z,E-isomer (Table IV). This alteration is exactly the reverse of the effect of applying the Z,Z-isomer.

TABLE IV

| Treatment in Plot | % of total catch indicated ratio[1] | | | | | | |
|---|---|---|---|---|---|---|---|
| | 1:0 | 9:1 | 3:1 | 1:1 | 1:3 | 1:9 | 0:1 |
| Z,E-isomer | 1 b | 4 b | 7 ab | 17 ab | 23 ab | 34 a | 14 ab |
| Control | 0 d | 10 c | 28 b | 59 a | 1 d | 0 d | 0 d |

[1]Means within a row followed by a common letter are not significantly different (P = 0.05) by Duncan's multiple range test.

EXAMPLE 6

Use of the invention causes the preference of male pinkspotted bollworm moths to be shifted away from the ratio of Z,Z- to Z,E-isomers which catches the most moths in untreated fields (9:1) and therefore is presumed to approximate the ratio found in the pheromone secretion of the female.

The test was conducted in Biloela, Queensland, Australia, during the period of Feb. 28 to Mar. 5. Test plots were 35×35 m separated by 600 m and were planted to short staple cotton. Treated plots contained 400 rubber stoppers treated with 5 mg each of the test isomer and pinned to the tops of the plants on a 2-meter grid (rate of ca. 5000 stoppers containing 25 g AI/ha). The control plot was left untreated. The ratio test consisted of 4 Delta traps/ratio baited with a rubber stopper treated with following ratios (Z,Z-: Z,E-): 1:0, 9:1, 3:1, 1:1, 1:3, 1:9, 0:1. Each bait contained 1 mg of the test ratio. Catches were recorded daily.

The results of the test (Table V) showed that the field treatment with the Z,E-isomer caused a significant shift in the preference of males to ratios containing unnatural percentages of the Z,E-isomer, although the shift in response in this species was less pronounced than with the pink bollworm: traps baited with the 1:1 and 1:3 ratios captured 25 and 23% of the total males caught while the 9:1 ratio caught 11%.

Fewer total moths were captured in the plot treated with the Z,Z-isomer (6% of the capture in the control plot) but the 9:1 ratio accounted for 53% of the total indicating no change in the preference of males for their natural ratio. This result was anticipated since the natural 9:1 ratio is close to the 1:0 ratio which is also quite attractive to this species.

TABLE V

| Treatment in field | Avg. catch/night for indicated ratio (Z,Z-:Z,E-)[1] | | | | | | |
|---|---|---|---|---|---|---|---|
| | 1:0 | 9:1 | 3:1 | 1:1 | 1:3 | 1:9 | 0:1 |
| Z,Z-isomer | 1 b | 4 a | 0 b | 1 b | 1 b | 0 b | 0 b |
| Z,E-isomer | 6 cd | 10 bc | 16 ab | 22 a | 23 a | 16 ab | 0 d |
| Control | 20 b | 98 a | 6 b | 6 b | 1 b | 1 b | 1 b |

[1]Means within rows followed by a common letter are not significantly different at the 0.05% level.

It is understood that the foregoing detailed description is given merely by way of illustration and that modification and variations may be made therein without departing from the spirit and scope of the invention.

Having thus described the invention, we claim:

1. A composition comprising a mixture of first and second pheromone dispensers selected from the group consisting of flake dispensers, hollow fibers, and microcapsules, wherein said first dispenser contains Z,Z- or Z,E-isomer of 7-11-hexadecadien-1-ol acetate in an amount sufficient to shift the preference of a male pink bollworm from a volume ratio of Z,Z-:Z,E-isomer naturally occurring in the pheromone emitted by a female pink bollworm and to a different volume ratio, and wherein said second dispenser contains an effective attractant amount of Z,Z- and Z,E-isomers of 7,11-hexadecadiene-1-ol acetate, wherein said Z,Z-:Z,E-isomer volume ratio in said second dispenser is about 75:25 to 99:1 when said first dispenser contains Z,Z-isomer, and wherein said Z,Z-:Z,E-isomer volume ratio in said second dispenser is about 25:75 to 1:99 when said first dispenser contains Z,E-isomer.

2. The composition of claim 1 further comprising an effective insecticidal amount of an insecticide for the pink bollworm.

3. A composition comprising a mixture of first and second pheromone dispensers selected from the group consisting of flake dispensers, hollow fibers, and microcapsules, wherein said first dispenser contains Z,E-isomer of 7,11-hexadecadien-1-ol acetate in an amount sufficient to shift the preference of a male pinkspotted bollworm from a volume ratio of Z,Z-:Z,E-isomer naturally occurring in the pheromone emitted by a female pinkspotted bollworm and to a different volume ratio, and wherein said second pheromone dispenser contains an effective attractant amount of Z,Z- and Z,E-isomers of 7,11-hexadecadien-1-ol acetate in a volume ratio of Z,Z-:Z,E-isomer of about 3:1 to 1:9.

4. The composition of claim 3 further comprising an effective insecticidal amount of an insecticide for the pinkspotted bollworm.

5. A method of shifting the preference of an adult male pink bollworm from the natural pheromone of a female pink bollworm, comprising:
   (a) treating a locus of pink bollworm males with Z,Z- or Z,E-isomer of 7,11-hexadecadien-1-ol acetate in an amount sufficient to shift the preference of the male pink bollworm from a volume ratio of Z,Z-:Z,E-isomer naturally occurring in the pheromone emitted by the female pink bollworm and to a different volume ratio, and
   (b) applying an effective attractant amount of Z,Z- and Z,E-isomers of 7,11-hexadecadien-1-ol acetate to the locus;
   wherein said Z,Z-:Z,E-isomer volume ratio in step (b) is about 75:25 to 99:1 when the treatment of step (a) is Z,Z-isomer, and said Z,Z-:Z,E-isomer volume ratio in step (b) is about 25:75 to 1:99 when the treatment of step (a) is Z,E-isomer.

6. The method of claim 5 wherein the treatment in step (a) is Z,E-isomer and the ratio of Z,Z-:Z,E-isomer in step (b) is about 90:10 to 99:1.

7. The method of claim 5 further comprising applying an effective insecticidal amount of an insecticide for the pink bollworm to the locus.

8. The method of claim 7 wherein the ratio of Z,Z-:Z,E-isomer in step (b) is about 90:10 to 99:1.

9. The method of claim 5 wherein the step of applying said effective amount of Z,Z- and Z,E-isomers in step (b) comprises placing traps in said locus baited with said effective amount of Z,Z- and Z,E-isomers.

10. A method of shifting the preference of an adult male pinkspotted bollworm from the natural pheromone of a female pinkspotted bollworm, comprising:
    (a) treating a locus of pinkspotted bollworm males with Z,E-isomer of 7,11-hexadecadien-1-ol acetate in an amount sufficient to shift the preference of the male pinkspotted bollworm from a volume ratio of Z,Z-:Z,E-isomer naturally occurring in the pheromone emitted by the female pinkspotted bollworm and to a different volume ratio, and
    (b) applying an effective attractant amount of Z,Z- and Z,E-isomers of 7,11-hexadecadien-1-ol acetate in a volume ratio of Z,Z-:Z,E-isomer of about 3:1 to 1:9 to the locus.

11. The method of claim 10 wherein the ratio of Z,Z-:Z,E-isomer in step (b) is about 1:1 to 1:3.

12. The method of claim 10 further comprising applying an effective insecticidal amount of an insecticide for the pinkspotted bollworm to the locus.

13. The method of claim 12 wherein the ratio of Z,Z-:Z,E-isomer in step (b) is about 1:1 to 1:3.

14. The method of claim 10 wherein the step of applying said effective amount of Z,Z- an Z,E-isomers in step (b) comprises placing traps in said locus baited with said effective amount of Z,Z- and Z,E-isomers.

* * * * *